United States Patent [19]
Hete et al.

[11] Patent Number: 5,694,923
[45] Date of Patent: Dec. 9, 1997

[54] PRESSURE CONTROL IN A BLOWER-BASED VENTILATOR

[75] Inventors: Bernie F. Hete, Trafford; Peter D. Hill, Monroeville; Michael J. Beiriger, Pittsburgh, all of Pa.

[73] Assignee: Respironics, Inc., Murraysville, Pa.

[21] Appl. No.: 697,831

[22] Filed: Aug. 30, 1996

[51] Int. Cl.⁶ ............................................. A61M 16/00
[52] U.S. Cl. ..................... 128/204.18; 128/204.21; 128/204.23
[58] Field of Search .................... 128/204.18, 204.21, 128/204.23, 204.26, 205.25, 207.18, 202.22

[56] References Cited

U.S. PATENT DOCUMENTS

| | | | |
|---|---|---|---|
| 5,148,802 | 9/1992 | Sanders et al. | 128/204.18 |
| 5,239,995 | 8/1993 | Estes et al. | 128/204.23 |
| 5,313,937 | 5/1994 | Zdrojkowski | 128/202.22 |
| 5,433,193 | 7/1995 | Sanders et al. | 128/204.18 |
| 5,535,738 | 7/1996 | Estes et al. | 128/204.23 |

Primary Examiner—Kimberly L. Asher
Assistant Examiner—Eric P. Raciti
Attorney, Agent, or Firm—Reed Smith Shaw & McClay

[57] ABSTRACT

A valving arrangement for use with or for a blower-based ventilator system, such as a pressure support ventilator, and a pressure support ventilator having such a valving arrangement, in which blower output can be controlled in such a manner that desired levels of pressure are able to be provided without excessive waste of blower output flow. In one preferred embodiment, a first valve is provided that serves to restrict blower flow, without venting the same from the system, along with a second valve for relieving pressure as needed. Also contemplated herein are methods for controlling such a valving arrangement.

25 Claims, 9 Drawing Sheets

PRESSURE CONTROL IN A BLOWER-BASED VENTILATOR

FIELD OF THE INVENTION

The present invention generally relates to ventilator systems, such as pressure support ventilators, and valve arrangements for use therewith or therefor.

BACKGROUND OF THE INVENTION

Historically, many individuals have required the use of pressure support ventilators in order to assist with respiratory problems, such as sleep apnea. Thus, over the years, a wide range of pressure support ventilators have been developed and produced that are designed to meet the needs of the individuals in question.

Essentially, the primary objective of a pressure support ventilator is to impart to a respiratory patient sufficient air (or gas) pressure in his or her airway so as to either preliminarily obviate the effect of any resistances or impedances within the patient's airway that might otherwise arise in the context of a patient's normal breathing patterns (e.g. sleep apnea) or even overcome airway resistances or impedances that might be of a more static nature (e.g. longer-term constrictions of the airway, or even lungs, caused by any of a number of possible physiological factors). As briefly discussed below, this impartation of pressure to a patient's airway has taken different forms over the years.

One basic form of pressure support that was developed initially was a so-called "continuous positive airway pressure", or "CPAP" support system, including those systems developed by Respironics, Inc., of Murrysville, Pa. This would involve the provision essentially of one constant pressure throughout a patient's entire breathing pattern. Although the single constant pressure was normally sufficient to overcome a patient's airway resistances or impedances (as discussed above), it was often found that a patient's ability to effectively exhale in such a context might be difficult.

An innovation over the above-described "CPAP", as developed by Respironics, Inc., was what was regarded as a "bi-level" support system ("BiPAP"). This involved the provision of suitable sensing components for detecting the periods of time during which a patient would either inhale or exhale. Consequently, the sensing components were utilized in such a way that, during inhalation, one given pressure could be provided to the patient, while during exhalation, another, notably reduced, pressure could be provided. Several U.S. patents describe this "bi-level" system in detail, including U.S. Pat. Nos. 5,433,193; 5,313,937; 5,239,995; and 5,148,802, all of which are hereby expressly incorporated by reference as if set forth in its entirety herein.

In further innovations, apparatus and methods were developed in which the air or gas pressure supplied to a patient in the context of a pressure support system could be variable, either depending on a preprogrammed algorithm that exacted a predetermined time-dependent pattern of pressures on the patient or specific, instantaneously monitored demands of the patient. A device along these lines is disclosed in U.S. Pat. No. 5,535,738, which is also hereby expressly incorporated by reference as if set forth in its entirety herein.

Generally, whether the pressure administered to a patient is intended to be virtually constant over given periods of time (as in a "BiPAP" system) or variable, there has typically been a need to monitor the pressure being provided to the patient with a feedback control system so that, if necessary, the pressure can be readjusted so as to conform to the desired output pressure. Typically, such feedback control has not involved adjustment of the blower motor, as there are logistical problems associated with this (such as imprecisions in changing the motor speed within a short period of time, for instance). Accordingly, many conventional systems have included a single pressure relief valve, situated between the blower outlet and the start of the "patient circuit" (i.e. that portion of the respiratory circuit that includes tubing, filters, water traps, valves, etc. that are regarded as being necessary for providing suitably conditioned air or gas to the patient in question), that serves to readjust the air or gas pressure in the respirator circuit in response to prompts from the feedback control system. Such a pressure relief valve would also be typically used for exhausting air and/or gas emanating from a patient upon exhaling (thereby causing a net "negative" flow in the respirator circuit, i.e. back towards the blower, which would be vented off through the pressure relief valve).

Since such pressure relief valves are typically embodied by proportional valves that open to merely vent a portion of the flow of the respirator circuit to the ambient atmosphere (or other predetermined remote location), it is essentially the case that they are only able to increase pressure within the system upon being further closed from an already open position, wherein a fully "open" position would result in maximum venting from the system (thereby resulting in decreased pressure in the patient circuit) and a fully "closed" position would result in minimal or nonexistent venting from the system (thereby resulting in increased pressure in the patient circuit).

Since, especially in the context of respiratory patients who may require increased airway pressure from time to time, it must often be assumed that an allowance must be made for increasing the pressure provided to the patient from a lower level, it was therefore often necessary, in the context of systems utilizing a pressure relief valve as discussed above, to keep the valve open during normal inhalations and exhalations of the patient, with the understanding that a sudden, instantaneous demand for greater pressure (as initiated, for example, by an unexpectedly occurring blockage or constriction in the patient's airway and as measured by appropriate pressure and/or flow sensors at the patient circuit), could be attended to by closing the pressure relief valve to the degree sufficient for providing the demanded pressure. Alternatively, and especially in the context of more continuous systems such as the "BiPAP", it would often merely be the case that a wide range of constant inhalation pressures (as provided by the system) had to be allowed for in manufacturing the systems in question, in view of their use among a wide variety of patients with widely varying static pressure requirements. In any case, in order to assure a sufficient margin of safety, there was often the consequence that tremendous levels of air or gas flow would be vented away by the pressure relief valve, to be "reined in" only in those instances where greater pressure (for the patient) would be required.

Thus, although the use of a single pressure relief valve, as discussed above, can offer stable, fast open-loop pressure control, its utility has been limited by the level of pressure and flow required from the blower fan, which itself has not been, and essentially cannot be, used for pressure control. High motor speeds in this context have the tendency of increasing bearing and motor loads (in proportion to the square of motor speed), while the resultant excessive flow has the tendency of wasting power since work needs to be done to the fluid to bring it up to pressure, only to release it to the atmosphere. It stands to note that the exhausting of large gas flows also tends to be very noisy.

Recent years have also seen the development of, and demands for, blower-based pressure support ventilators that provide considerably larger pressures than conventional devices. Since this would normally result in the provision of ventilators having blowers that would subsequently provide astronomically excessive levels of flow that, in the context of single pressure-relief valve arrangements as discussed above, would result in tremendous wasted flow and unprecedentedly excessive noise levels (from exhaust), a need has arisen to efficiently regulate respirator flow and pressure in a manner that minimizes waste while still providing the patient with adequate respiratory support.

SUMMARY OF THE INVENTION

In accordance with at least one preferred embodiment of the present invention, an arrangement is contemplated in which blower output can be controlled in such a manner that the desired levels of pressure are still able to be provided, without wasting blower output flow.

In accordance with a preferred embodiment of the present invention, a first valve is provided that serves to restrict blower flow, without venting the same from the system, along with a second valve for relieving pressure as needed.

In accordance with a preferred embodiment of the present invention, the pressure and flow are adjustable as they have been previously, with the added advantage that the aforementioned first valve is also continuously and proportionally adjustable in such a manner that, upon a demand being placed on the system for increased flow, the blower output curve will be shifted so as to result in minimal excess flow in response to the pressure also simultaneously demanded.

In summary, one aspect of the present invention broadly contemplates apparatus for delivering pressurized gas to the airway of a patient, the apparatus comprising:

a gas flow generator arrangement for providing a flow of the gas;

a conduit arrangement for delivery of the gas flow to the airway of the patient;

an arrangement for controlling the pressure of the gas flow delivered to the airway of the patient;

the controlling arrangement comprising:

an arrangement for restricting the gas flow in the conduit arrangement prior to its being delivered to the airway of the patient;

an arrangement for selectively venting a portion of the gas flow away from the conduit arrangement prior to its being delivered to the airway of the patient; and an arrangement for selectively actuating the restricting arrangement and the venting arrangement in a manner to substantially minimize the quantity of gas flow vented away from the conduit arrangement prior to its being delivered to the airway of the patient.

In another aspect, the present invention broadly contemplates, in apparatus for delivering pressurized gas to the airway of a patient, such apparatus comprising a gas flow generator arrangement for providing a flow of the gas and a conduit arrangement for delivery of the gas flow to the airway of the patient; an arrangement for controlling the pressure of the gas flow delivered to the airway of the patient, the controlling arrangement comprising:

an arrangement for restricting the gas flow in the conduit arrangement prior to its being delivered to the airway of the patient;

an arrangement for selectively venting a portion of the gas flow away from the conduit arrangement prior to its being delivered to the airway of the patient; and an arrangement for selectively actuating the restricting arrangement and the venting arrangement in a manner to substantially minimize the quantity of gas flow vented away from the conduit arrangement prior to its being delivered to the airway of the patient.

In yet another aspect, the present invention broadly contemplates a method of controlling the pressure of gas flow delivered to the airway of a patient in apparatus for delivering pressurized gas to the airway of a patient, such apparatus comprising a gas flow generator arrangement for providing a flow of the gas and a conduit arrangement for delivery of the gas flow to the airway of the patient; the method comprising the steps of:

restricting the gas flow in the conduit arrangement prior to its being delivered to the airway of the patient;

selectively venting a portion of the gas flow away from the conduit arrangement prior to its being delivered to the airway of the patient; and selectively actuating the restricting arrangement and the venting arrangement in a manner to substantially minimize the quantity of gas flow vented away from the conduit arrangement prior to its being delivered to the airway of the patient.

BRIEF DESCRIPTION OF THE DRAWINGS

The present invention and its presently preferred embodiments will be better understood by way of reference to the detailed disclosure herebelow and to the accompanying drawings, wherein.

DETAILED DESCRIPTION OF THE PREFERRED EMBODIMENTS

Figure 1:
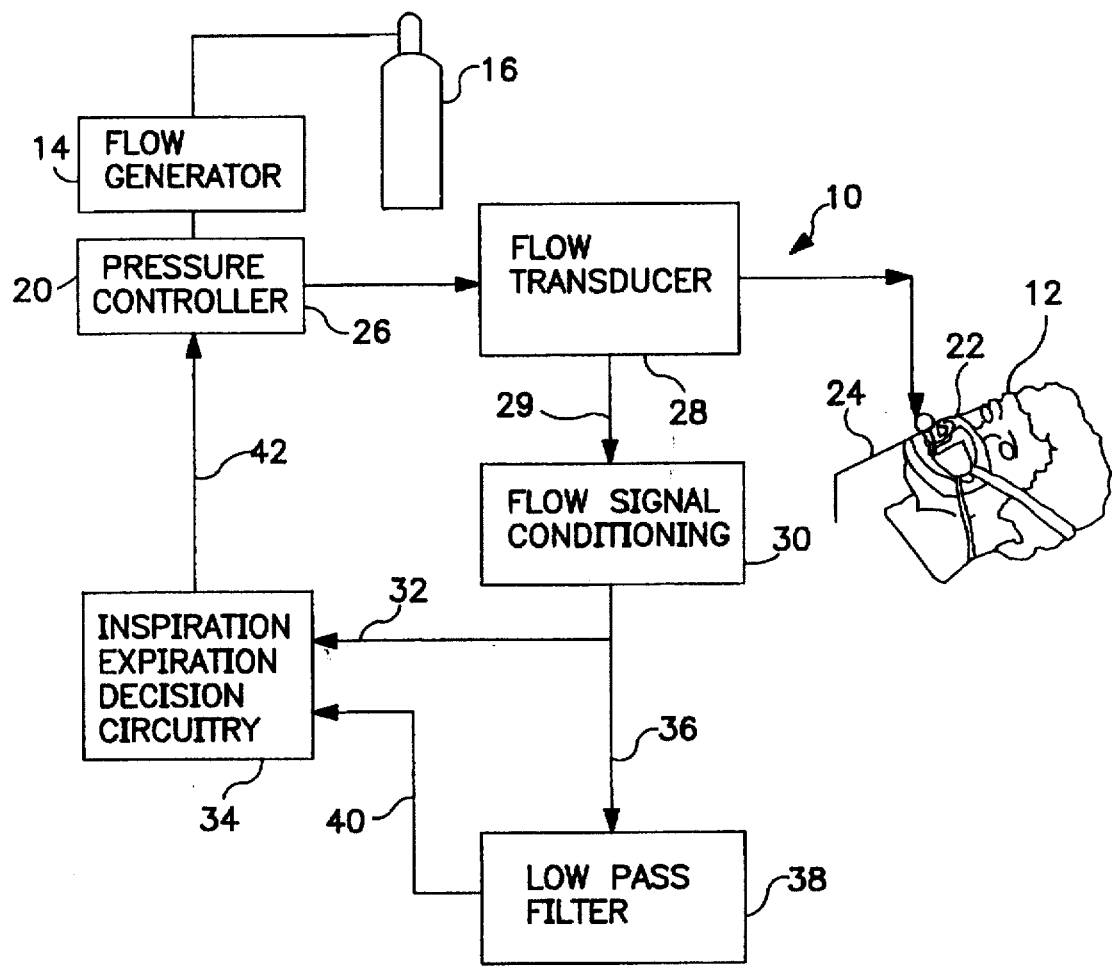
FIG. 1 is a functional block diagram of a conventional apparatus having components, and being operable by at least portions of a method, that may be utilized in accordance with the embodiments of the present invention.
Figure 2:
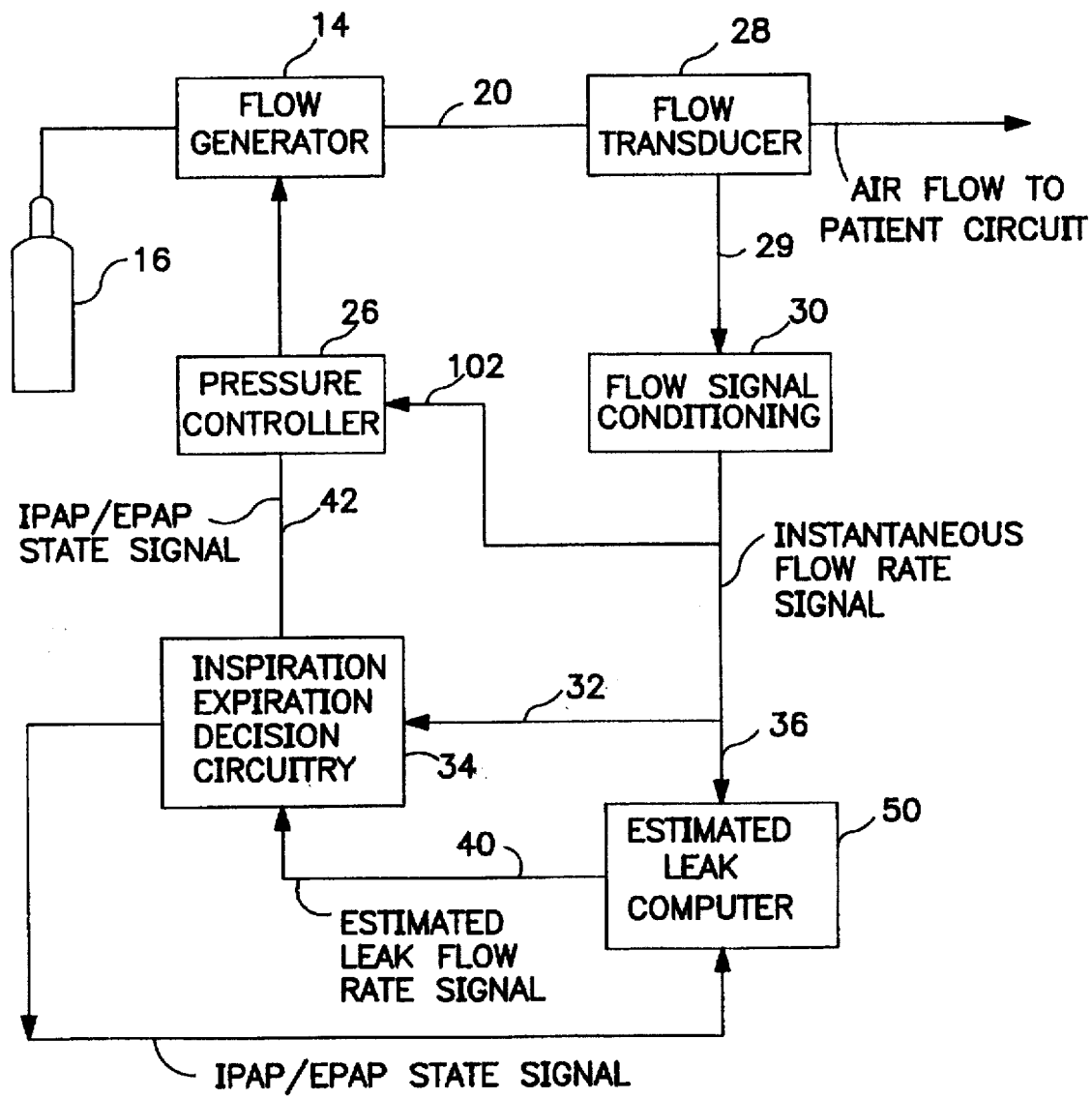
FIG. 2 is a functional block diagram showing an alternative embodiment.
Figure 3:
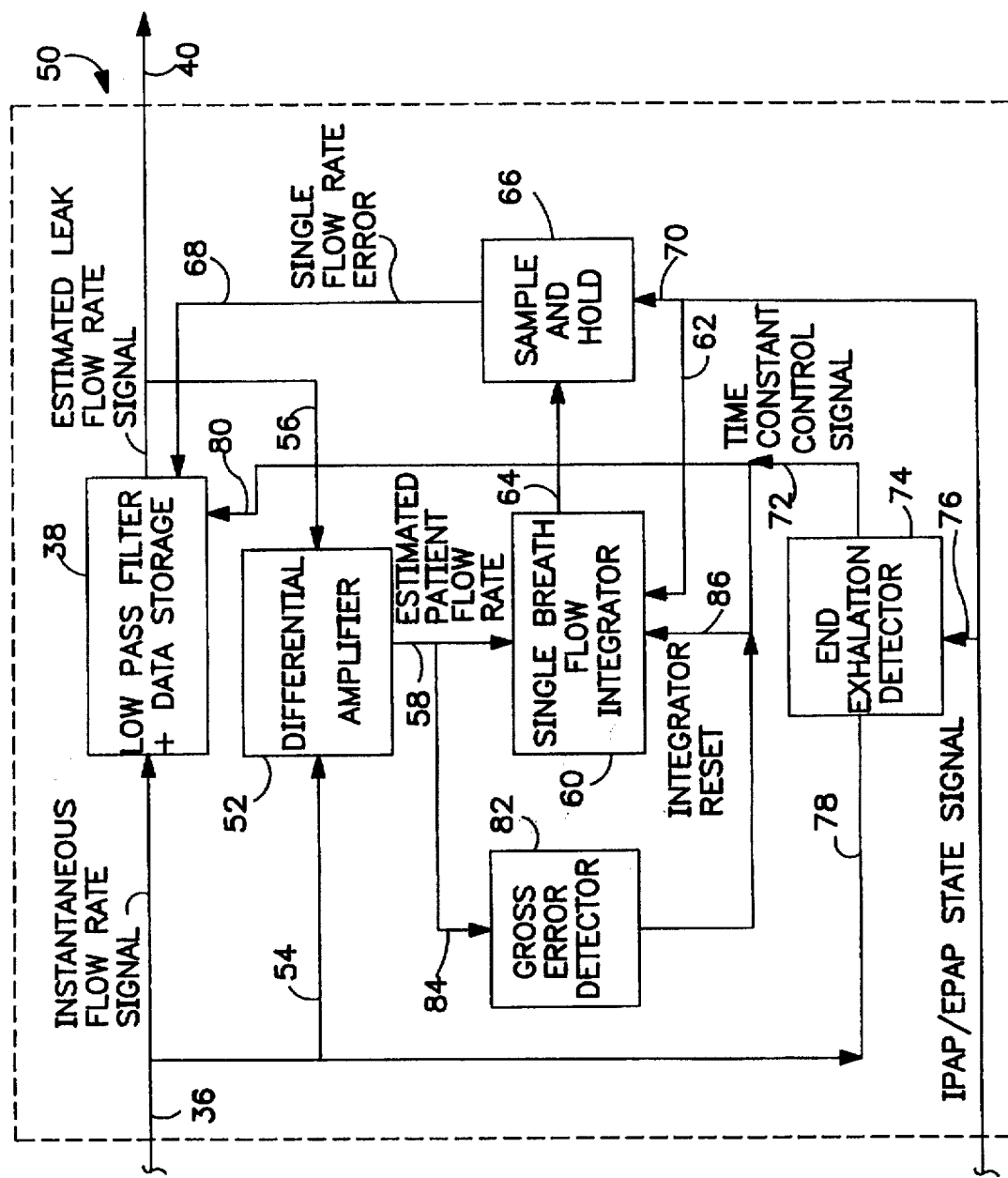
FIG. 3 is a functional block diagram of the Estimated Leak Computer of FIG. 2.

The disclosure presently will turn to a description of a conventional bi-level apparatus, as illustrated in FIGS. 1–3, that possesses components, and contemplates manipulations of the same, that may be utilized in accordance with at least one presently preferred embodiment of the present invention. Other details regarding such conventional apparatus may be found in the U.S. Patents listed at the beginning of this specification, especially U.S. Pat. No. 5,148,802. It is to be understood that the conventional bi-level apparatus described and illustrated with respect to FIGS. 1–3 is provided as an example and is in no way meant to limit the spirit and scope of the invention.

Apparatus 10 in FIG. 1 is operable according to a process for delivering breathing gas, such as air, alternately at relatively higher and lower pressures (i.e., equal to or above ambient atmospheric pressure) to a patient 12 for treatment of a given respiratory condition, such as the condition known as sleep apnea.

Apparatus 10 comprises a gas flow generator 14 (e.g., a blower) which receives breathing gas from any suitable source, such as a pressurized bottle 16 or the ambient atmosphere, for example. The gas flow from flow generator 14 (which, for all intents and purposes, can be considered to be a pressure generator) is passed via a delivery conduit 20 to a breathing appliance such as a mask 22 of any suitable known construction which is worn by patient 12. The mask 22 may preferably be a nasal mask or a full face mask 22 as shown. Other breathing appliances which may be used in lieu of a mask include nasal cannulae, an endotracheal tube, or any other suitable appliance for interfacing between a source of breathing gas and a patient, consistent with the desired effect to be achieved through use of the apparatus 10.

The mask 22 includes a suitable exhaust port means, schematically indicated at 24, for exhaust of breathing gases during expiration. Exhaust port 24 preferably is a continuously open port which imposes a suitable flow resistance upon exhaust gas flow to permit a pressure controller 26, located in line with conduit 20 between flow generator 14 and mask 22, to control the pressure of air flow within conduit 20 and thus within the airway of the patient 12. The flow via exhaust port 24 is one component, and typically the major component of the overall system leakage, which is an important parameter of system operation. In an alternative embodiment to be discussed hereinbelow, it has been found that a non-rebreathing valve may be substituted for the continuously open port 24.

The pressure controller 26 is operative to control the pressure of breathing gas within the conduit 20 and thus within the airway of the patient. Pressure controller 26 is located downstream of flow generator 14 and may take the form of an adjustable valve which provides a flow path which is open to the ambient atmosphere via a restricted opening, the valve being adjustable to maintain a constant pressure drop across the opening for all flow rates and thus a constant pressure within conduit 20.

Also interposed in line with conduit 20, downstream of pressure controller 26, is a suitable flow transducer 28 which generates an output signal that is fed as indicated at 29 to a flow signal conditioning circuit 30 for derivation of a signal proportional to the instantaneous flow rate of breathing gas within conduit 20 to the patient.

It will be appreciated that flow generator 14 is not necessarily a positive displacement device. It may be, for example, a blower which creates a pressure head within conduit 20 and provides air flow only to the extent required to maintain that pressure head in the presence of patient breathing cycles, the exhaust opening 24, and action of pressure controller 26 as above described. Accordingly, when the patient is exhaling, peak exhalation flow rates from the lungs may far exceed the flow capacity of exhaust port 24. As a result, exhalation gas backflows within conduit 20 through flow transducer 28 and toward pressure controller 26, and the instantaneous flow rate signal from transducer 28 thus will vary widely within a range from relatively large positive (i.e. toward the patient) flow to relatively large negative (i.e. from the patient) flow.

The instantaneous flow rate signal from flow signal conditioning circuitry 30 is fed as indicated at 32 to a decision module 34, a known comparator circuit for example, and is additionally fed as indicated at 36 to a low pass filter 38. Low pass filter 38 has a cut-off frequency low enough to remove from the instantaneous flow rate input signal most variations in the signal which are due to normal breathing. Low pass filter 38 also has a long enough time constant to ensure that spurious signals, aberrant flow patterns and peak instantaneous flow rate values will not dramatically affect system average flow. That is, the time constant of low pass filter 38 is selected to be long enough that it responds slowly to the instantaneous flow rate signal input. Accordingly, most instantaneous flow rate input signals which could have a large impact on system average flow in the short term have a much smaller impact over a longer term, largely because such instantaneous flow rate signal components will tend to cancel over the longer term. For example, peak instantaneous flow rate values will tend to be alternating relatively large positive and negative flow values corresponding to peak inhalation and exhalation flow achieved by the patient during normal spontaneous breathing. The output of low pass filter 38 thus is a signal which is proportional to the average flow in the system, and this is typically a positive flow which corresponds to average system leakage (including flow from exhaust 24) since, as noted, inhalation and exhalation flow cancel for all practical purposes.

The average flow signal output from the low pass filter 38 is fed as indicated at 40 to decision circuitry 34 where the instantaneous flow rate signal is continually compared to the system average flow signal. The output of the decision circuitry 34 is fed as a drive signal indicated at 42 to control the pressure controller 26. The pressure magnitude of breathing gas within conduit 20 thus is coordinated with the spontaneous breathing effort of the patient 12, as follows.

When the patient begins to inhale, the instantaneous flow rate signal goes to a positive value above the positive average flow signal value. Detection of this increase in decision circuitry 34 is sensed as the start of patient inhalation. The output signal from decision circuitry 34 is fed to pressure controller 26 which, in response, provides higher pressure gas flow within conduit 20 and thus higher pressure within the airway of the patient 12. This is the higher magnitude pressure value of our bi-level CPAP system and is referred to hereinbelow as IPAP (inhalation positive airway pressure). During inhalation, the flow rate within conduit 20 will increase to a maximum and then decrease as inhalation comes to an end.

At the start of exhalation, air flow into the patient's lungs is nil and as a result the instantaneous flow rate signal will be less than the average flow rate signal which, as noted is a relatively constant positive flow value. The decision circuitry 34 senses this condition as the start of exhalation and provides a drive signal to pressure controller 26 which, in response, provides gas flow within conduit 20 at a lower pressure which is the lower magnitude pressure value of the bi-level CPAP system, referred to hereinbelow as EPAP (exhalation positive airway pressure). As has been noted hereinabove the range of EPAP pressures may include ambient atmospheric pressure. When the patient again begins spontaneous inhalation, the instantaneous flow rate signal again increases over the average flow rate signal, and the decision circuitry once again feeds a drive signal to pressure controller 26 to reinstitute the IPAP pressure.

System operation as above specified requires at least periodic comparison of the input signals 32 and 40 by decision circuitry 34. Where this or other operations are described herein as continual, the scope of meaning to be ascribed includes both continuous (i.e. uninterrupted) and periodic (i.e. at discrete intervals).

As has been noted, the system 10 has a built-in leakage via exhaust port 24 thus assuring that the average flow signal will be at least a small positive flow. During inhalation, the flow sensed by the flow transducer will be the sum of exhaust flow via port 24 and all other system leakage downstream of transducer 28, and inhalation flow within the airway of the patient 12. Accordingly, during inhalation the instantaneous flow rate signal as conditioned by conditioning module 30, will reliably and consistently reflect inhalation flow exceeding the average flow rate signal. During exhalation flow from the lungs of the patient far exceeds the flow capacity of exhaust port 24. Accordingly, exhalation air backflows within conduit 20 past transducer 28 and toward pressure controller 26. Since pressure controller 26 is operable to maintain set pressure, it will act in response to flow coming from both the patient and the flow generator to open an outlet port sufficiently to accommodate the additional flow volume and thereby maintain the specified set pressure as determined by action of decision circuitry 34.

In both the inhalation and exhalation cycle phases, the pressure of the gas within conduit 20 exerts a pressure within the airway of the patient to maintain an open airway and thereby alleviate airway constriction.

In practice, it may be desirable to provide a slight offset in the switching level within decision circuitry 34 with respect to the average flow rate signal, so that the system does not prematurely switch from the low pressure exhalation mode to the higher pressure inhalation mode. That is, a switching setpoint offset in the positive direction from system average flow may be provided such that the system will not switch to the IPAP mode until the patient actually exerts a significant spontaneous respiratory effort of a minimum predetermined magnitude. This will ensure that the initiation of inhalation is completely spontaneous and not forced by an artificial increase in airway pressure. A similar switching setpoint offset may be provided when in the IPAP mode to ensure the transition to the lower pressure EPAP mode will occur before the flow rate of air into the lungs of the patient reaches zero (i.e. the switch to EPAP occurs slightly before the patient ceases inhalation.) This will ensure that the patient will encounter no undue initial resistance to spontaneous exhalation.

From the above description, it will be seen that a method of treating sleep apnea is provided according to which the airway pressure of the patient is maintained at a higher positive pressure during inspiration and a relatively lower pressure during expiration, all without interference with the spontaneous breathing of the patient. The described apparatus is operable to provide such treatment for sleep apnea or other patients by providing a flow of breathing gas to the patient at positive pressure, and varying the pressure of the air flow to provide alternatively high and low pressure within the airway of the patient coordinated with the patient's spontaneous inhalation and exhalation.

To provide pressure control, the flow rate of breathing gas to the patient is detected and processed to continually provide a signal which is proportional to the instantaneous flow rate signal is further processed to eliminate variations attributable to normal patient respiration and other causes thus generating a signal which is proportional to the average or steady state system gas flow. The average flow signal is continually compared with the instantaneous flow signal as a means to detect the state of the patient's spontaneous breathing versus average system flow. When instantaneous flow exceeds the average flow, the patient is inhaling, and in response the pressure of gas flowing to the patient is set at a selected positive pressure, to provide a corresponding positive pressure within the airway of the patient. When comparison of the instantaneous flow rate signal with the average flow signal indicates the patient is exhaling, as for example when the instantaneous flow signal indicates flow equal to or less than the average flow, the pressure of breathing gas to the patient is adjusted to a selected lower pressure to provide a corresponding lower pressure within the airway of the patient.

In an alternative embodiment as shown in FIGS. 2 and 3, the low pass filter 38 is replaced by an estimated leak computer which includes a low pass filter as well as other functional elements as shown in FIG. 3. The remainder of the system as shown in FIG. 2 is similar in most respects to the system shown in FIG. 1. Accordingly, like elements are identified by like numbers, and the description hereinabove of FIG. 1 embodiment also applies generally to FIG. 2.

By using the operative capability of the estimated leak computer 50, as described hereinbelow, it is possible to adjust the reference signal which is fed to decision circuitry 34 on a breath by breath basis rather than merely relying on long term average system flow. To distinguish this new reference signal from average system flow it will be referred to hereinbelow as the estimated leak flow rate signal or just the estimate leak signal.

As was noted hereinabove, the average system flow rate reference signal changes very slowly due to the long time constant of the low pass filter 38. This operative feature was intentionally incorporated to avoid disturbance of the reference signal by aberrant instantaneous flow rate signal incurred such as erratic breathing patterns. While it was possible to minimize the impact of such aberrations on the average flow rate reference signal, the average flow signal did nevertheless change, although by small increments and only very slowly in response to disturbances. Due to the long time constant of the low pass filter, such changes in the reference signal even if transitory could last for a long time.

Additionally, even a small change in the reference signal could produce a very significant effect on system triggering. For example, since the objective is to trigger the system to the IPAP mode when inhalation flow just begins to go positive, small changes in the reference signal could result in relatively large changes in the breathing effort needed to trigger the system to the IPAP mode. In some instances the change in reference signal could be so great that with normal breathing effort the patient would be unable to trigger the system. For example, if the system were turned on before placement of the mask on the face of the patient, the initial free flow of air from the unattached mask could result in a very large magnitude positive value for initial average system flow. If such value were to exceed the maximum inspiratory flow rate achieved in spontaneous respiration by the patient, the system would never trigger between the IPAP and EPAP modes because the decision circuitry would never see an instantaneous flow rate signal greater than the average flow rate signal, at least not until a sufficient number of normal breathing cycles after application of the mask to the patient to bring the reference signal down to a value more closely commensurate with the actual system leak in operation. As has been noted, with the low pass filter this could take a rather long time, during which time the patient would be breathing spontaneously against a uniform positive pressure. This would be tantamount to conventional CPAP and not at all in keeping with the present invention.

In addition to the embodiment based on a reference signal derived from estimated leak flow rate on a breath by breath basis which is controlled totally by spontaneous patient breathing, two further modes of operation also are possible, one being spontaneous timed operation in which the system automatically triggers to the IPAP mode for just long enough to initiate patient inspiration if the system does not sense inspiratory effort within a selected time after exhalation begins. To accomplish this, a timer is provided which is reset at the beginning of each patient inspiration whether the inspiratory cycle was triggered spontaneously or by the timer itself. Thus, only the start of inspiration is initiated by the timer. The rest of the operating cycle in this mode is controlled by spontaneous patient breathing and the circuitry of the system to be described.

A further mode of operation is based purely on timed operation of the system rather than on spontaneous patient breathing effort, but with the timed cycles coordinated to spontaneous patient breathing. The patient must do the coordination. The circuit timing is completely independent of patient.

Referring to FIG. 3, the estimated leak computer 50 includes the low pass filter 38' as well as other circuits which are operative to make corrections to the estimated leak flow rate signal based on on-going analysis of each patient breath. A further circuit is provided which is operative to adjust the estimated leak flow rate signal quickly after major changes in system flow such as when the blower has been running prior to the time when the mask is first put on the patient, or after a major leak the system has either started or has been shut off.

The low pass filter 38' also includes a data storage capability whose function will be described hereinbelow.

The low pass filter 38' operates substantially as described above with reference to FIG. 1 in that it provides a long term average of system flow which is commensurate with steady state system leakage including the flow capacity of the exhaust port 24. This long term average is operative in the FIG. 3 embodiment to adjust the estimated leak flow rate reference signal only when system flow conditions are changing very slowly.

To provide breath by breath analysis and adjustment of the reference signal, a differential amplifier 52 receives the instantaneous flow rate signal as indicated at 54, and the estimated leak signal output from low pass filter 38' as indicated at 56.

The output of differential amplifier 52 is the difference between instantaneous flow rate and estimated leak flow rate, or in other words estimated instantaneous patient flow rate. This will be clear upon considering the instantaneous flow is the sum of patient flow plus actual system leakage. The estimated patient flow signal output from differential amplifier 52 is provided as indicated at 58 to a flow integrator 60 which integrates estimate patient flow breath by breath beginning and ending with the trigger to IPAP. Accordingly, an additional input to the flow integrator 60 is the IPAP/EPAP state signal as indicated at 62. The IPAP/EPAP state signal is the same as the drive signal provided to pressure controller 26; that is, it is a signal indicating of the pressure state, as between IPAP and EPAP, of the system. The state signal thus may be used to mark the beginning and end of each breath for purposes of breath by breath integration by integrator 60.

If the estimated leak flow rate signal from low pass filter 38' is equal to the true system leak flow rate, and if the patient's inhaled and exhaled volumes are identical for a given breath (i.e. total positive patient flow equals total negative patient flow for a given breath), then the integral calculated by integrator 60 will be zero and no adjustment of estimated leak flow rate will result. When the integral calculated by integrator 60 is non-zero, the integral value in the form of an output signal from integrator 60 is provided as indicated at 64 to a sample and hold module 66. Of course, even with a zero value integral, an output signal may be provided to module 66, but the ultimate result will be adjustment of the estimated leak flow rate signal.

A non-zero integral value provided to module 66 is further provided to module 38' as indicated at 68 with each patient breath by operative action of the IPAP/EPAP state signal upon module 66 as indicated at 70. The effect of a non-zero integral value and in the direction which would reduce the integral value towards zero on the next breath if all other conditions remain the same.

With this system, if the patient's net breathing cycle volume is zero, and if the system leak flow rate changes, the integrator circuit will compensate for the change in the leak flow rate by incremental adjustments to the estimated leak flow rate within about ten patient breaths.

The integrator circuit 60 also will adjust the estimated leak flow rate signal in response to no-zero net volume in a patient breathing cycle. It is not unusual for a patient's breathing volume to be non-zero. For example, a patient may inhale slightly more on each breath than he exhales over several breathing cycles, and then follow with a deeper or fuller exhalation. In this case, the integrator circuit would adjust the estimated leak flow rate signal as if the actual system leak rate had changed; however, since the reference signal correction is only about one tenth as large as would be required to make the total correction in one breath, the reference signal will not change appreciable over just one or two breaths. Thus, the integrator circuit accommodates both changes in system leakage and normal variations in patient breathing patters. The integrator circuit normally would be active, for example, during rapid patient breathing.

An end exhalation module 74 is operative to calculate another data component for use in estimating the system leak flow rate as follows. The module 74 monitors the slope of the instantaneous flow rate wave form. When the slope value is near zero during exhalation (as indicated by the state signal wave form remains small after more than one second into the respiratory phase, the indication is that exhalation has ended and that the net flow rate at this point thus is the leak flow rate. However, if estimated patient flow rate is non-zero at the same time, one component of the instantaneous flow rate signal must be patient flow. When these conditions are met, the circuit adjust the estimated leak flow rate slowly in a direction to move estimated patient flow rate toward zero to conform to instantaneous patient flow conditions expected at the end of exhalation. The adjustment to estimate leak flow rate is provided as an output from module 74 to low pass filter 38' as indicated at 80. When this control mechanism takes effect, it disables the breath by breath volume correction capability of integrator circuit 60 for that breath only.

The output of module 74 is a time constant control signal which is provided to low pass filter 38' to temporarily shorten the time constant thereof for a sufficient period to allow the estimated leak flow rate to approach the instantaneous flow rate signal at that specific instant. It will be noted that shortening the low pass filter time constant increases the rapidity with which the low pass filter output (a system average) can adjust toward the instantaneous flow rate signal input.

Another component of estimated leak flow rate control is a gross error detector 82 which acts when the estimated patient flow rate, provided thereto as indicate at 84, is away from zero for more than about 5 seconds. Such a condition may normally occur, for example, when the flow generator 14 is running before mask 22 is applied to the patient. This part of the control system is operative to stabilize operation quickly after major changes in the leak rate occur.

In accordance with he above description, it will be seen that low pass filter 38' acts on the instantaneous flow rate signal to provide an output corresponding to average system flow, which is system leakage since patient inspiration and expiration over time constitutes a net positive flow of zero. With other enhancements, as described, the system average flow can be viewed as an estimate of leakage flow rate.

The differential amplifier 52 processes the instantaneous flow rate signal and the estimated leak flow rate signal to provide an estimated patient flow rate signal which is integrated and non-zero values of the integral are fed back to module 38' to adjust the estimated leak flow rate signal on a breath by breath basis. The integrator 60 is rest by the IPAP/EPAP state signal via connection 62.

Two circuits are provided which can override the integrator circuit, including end exhalation detector 74 which provides an out put to adjust the time constant of low pass filter 38' and which also is provided as indicated at 86 to reset integrator 60. Gross error detector 82 is also provided to process estimated patient flow rate and to provide an adjustment to estimated leak flow rate under conditions as specified. The output of module 82 also is utilized as an integrator reset signal as indicated at 86. It will be noted that the integrator 60 is reset with each breath of the patient if, during that breath, it is ultimately overridden by module 74 or 8 2. Accordingly, the multiple reset capabilities for integrator 60 as described are required.

In operation, the system may be utilized in a spontaneous triggering mode, a spontaneous/timed mode or a purely timed mode or operation. In spontaneous operation, decision circuitry 34 continuously compares the instantaneous flow rate with estimated leak flow rate. If the system is in the EPAP state or mode, it remains there until instantaneous flow rate exceeds estimated leak flow rate by approximately 40 cc per second. When this transition occurs, decision circuitry 34 triggers the system into the IPAP mode for 150 milliseconds. The system will then normally remain the IPAP mode as the instantaneous flow rate to the patient will continue to increase during inhalation due to spontaneous patient effort and the assistance of the increased IPAP pressure.

After the transition to the IPAP mode in each breath, a temporary offset is added to the estimated leak flow rate reference signal. The offset is proportional to the integral of estimated patient flow rate beginning at initiation of the inspiratory breath so that it gradually increases with time during inspiration at a rate proportional to the patient's inspiratory flow rate. Accordingly, the flow rate level above estimated leak flow needed to keep the system in the IPAP mode during inhalation decreases with time from the beginning of inhalation and in proportion to the inspiratory flow rate. With this enhancement, the longer an inhalation cycle continues, the larger is the reference signal below which instantaneous flow would have to decrease in order to trigger the EPAP mode. For example, if a patient inhales at a constant 500 cc per second until near the end of inspiration, a transition to EPAP will occur when his flow rate drops to about 167 cc per second after one second, or 333 cc per second after two seconds, or 500 cc per second after three seconds, and so forth. For a patient inhaling at a constant 250 cc per second, the triggers would occur at 83, 167 and 250 cc per second at one, two and three seconds into IPAP, respectively.

In this way, the EPAP trigger threshold comes up to meet the inspiratory flow rate with the following benefits. First it becomes easier and easier to end the inspiration cycle with increasing time into the cycle. Second, if a leak develops which causes an increase instantaneous flow sufficient to trigger the system into the IPAP mode, this system will automatically trigger back to the EPAP mode after about 3.0 seconds regardless of patient breathing effort. This would allow the volume-based leak correction circuit (i.e. integrator 60) to act as if it is activated with each transition to the IPAP mode. Thus, if a leak develops suddenly, there will be a tendency toward automatic triggering rather than spontaneous operation for a few breaths, but the circuit will not be locked into the IPAP mode.

Upon switching back to the EPAP mode, the trigger threshold will remain above the estimated leak flow rate for approximately 500 milliseconds to allow the system to remain stable in the EPAP mode without switching again while the respective flow rates are changing. After 500 milliseconds, the trigger threshold offset is reset to zero to await the next inspiratory effort.

The normal state for the circuit is for it to remain in the EPAP mode until an inspiratory effort is made by the patient. The automatic corrections and adjustments to the reference signal are effective to keep the system from locking up in the IPAP mode and to prevent auto-triggering while at the same time providing a high level of sensitivity to inspiratory effort and rapid adjustment for changing leak conditions and breathing patterns.

In the spontaneous/timed mode of operation, the system performs exactly as above described with reference to spontaneous operation, except that it allows selection of a minimum breathing rate to be superimposed upon the spontaneous operating mode. If the patient does not make an inspiratory effort within a predetermined time, the system will automatically trigger to the IPAP mode for 200 milliseconds. The increased airway pressure for this 200 milliseconds will initiate patient inspiration and provide sufficient time that spontaneous patient flow will exceed the reference signal so that the rest of the cycle may continue in the spontaneous mode as above described. The breaths per minute timer is reset by each trigger to IPAP whether the transition was triggered by the patient or by the timer itself.

In the timed operating mode, all triggering between IPAP and EPAP modes is controlled by a timer with a breath per minute control being used to select a desired breathing rate from, for example, 3 to 30 breaths per minute. If feasible, the selected breathing rate is coordinated to the patient's spontaneous breathing rate. The percent IPAP control is used to set the fraction of each breathing cycle to be spent in the IPAP mode. For example, if the breaths per minute control is set to 10 breaths per minute (6 seconds per breath) and the percent IPAP control is set to 33%, then the flow generator will spend, in each breathing cycle, two seconds in IPAP and four seconds in EPAP.

The disclosure now turns to discussion of an arrangement, according to at least one preferred embodiment of the present invention, that can be utilized in the general framework of an apparatus such as that described and illustrated with respect to FIGS. 1–3 or in other contexts, including those discussed in the "Background" section of this disclosure and/or as set forth in any of the U.S. patents cited therein.

Figure 4:
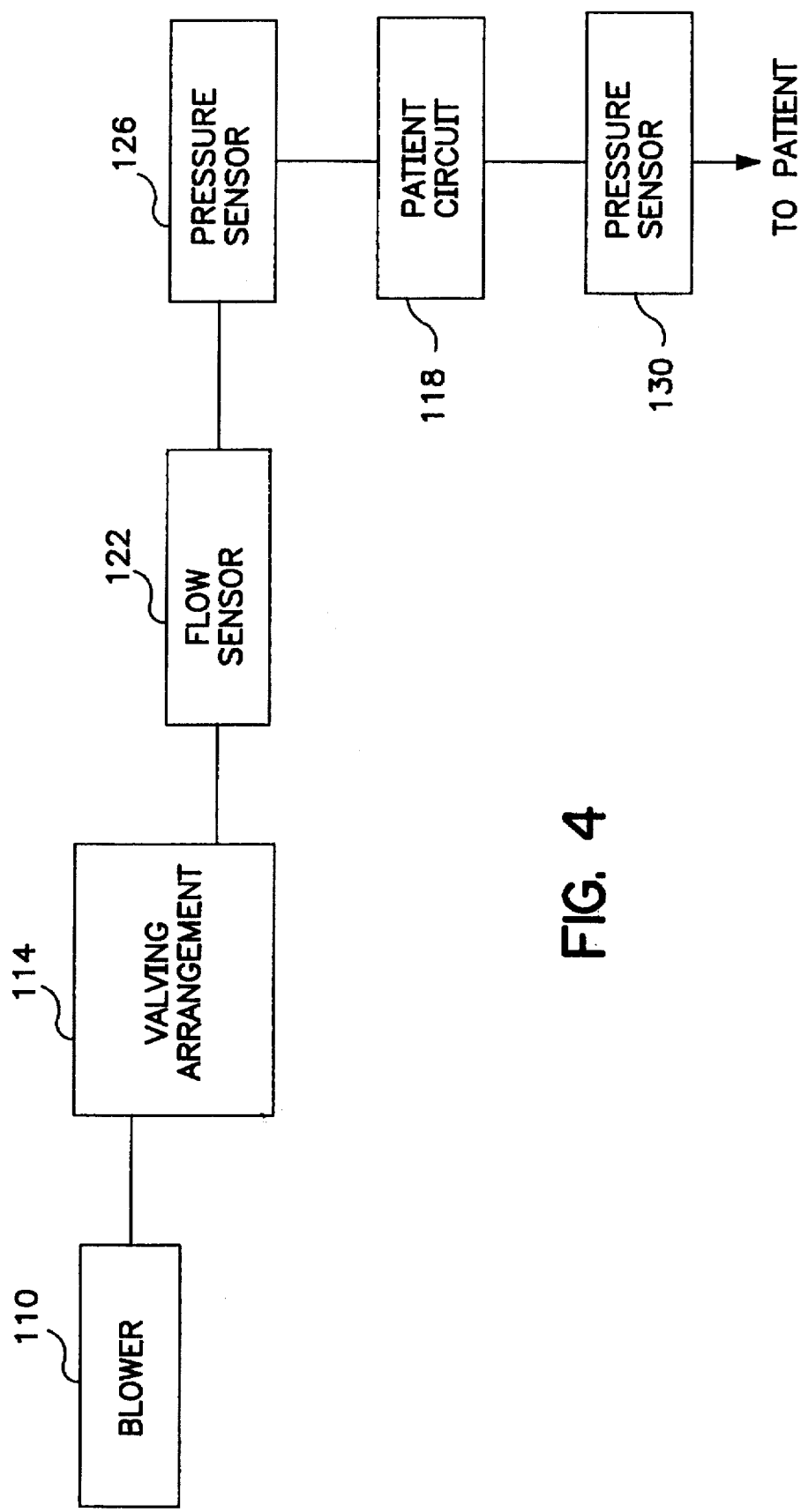
FIG. 4 schematically illustrates components of a respirator circuit according to at least one preferred embodiment of the present invention.

In FIG. 4, there is schematically illustrated a blower 110 connected to a valving arrangement 114 designed in accordance with at least one embodiment of the present invention. Generally, such blowers are well-known to those of ordinary skill in the art and will not be discussed in further detail herein. Also illustrated in FIG. 4 is a patient circuit 118, a concept which would also appear to be well-known to those of ordinary skill in the art. Indicated at 122, 126 and 130, respectively, are suitable devices for measuring flow rate, "outlet pressure" (i.e., the pressure present in the air stream prior to entering the patient circuit) and the "patient pressure" (i.e., the pressure present in the air stream prior to the same being directed to the patient's mask so as to be inhaled by the patient).

Figure 5:
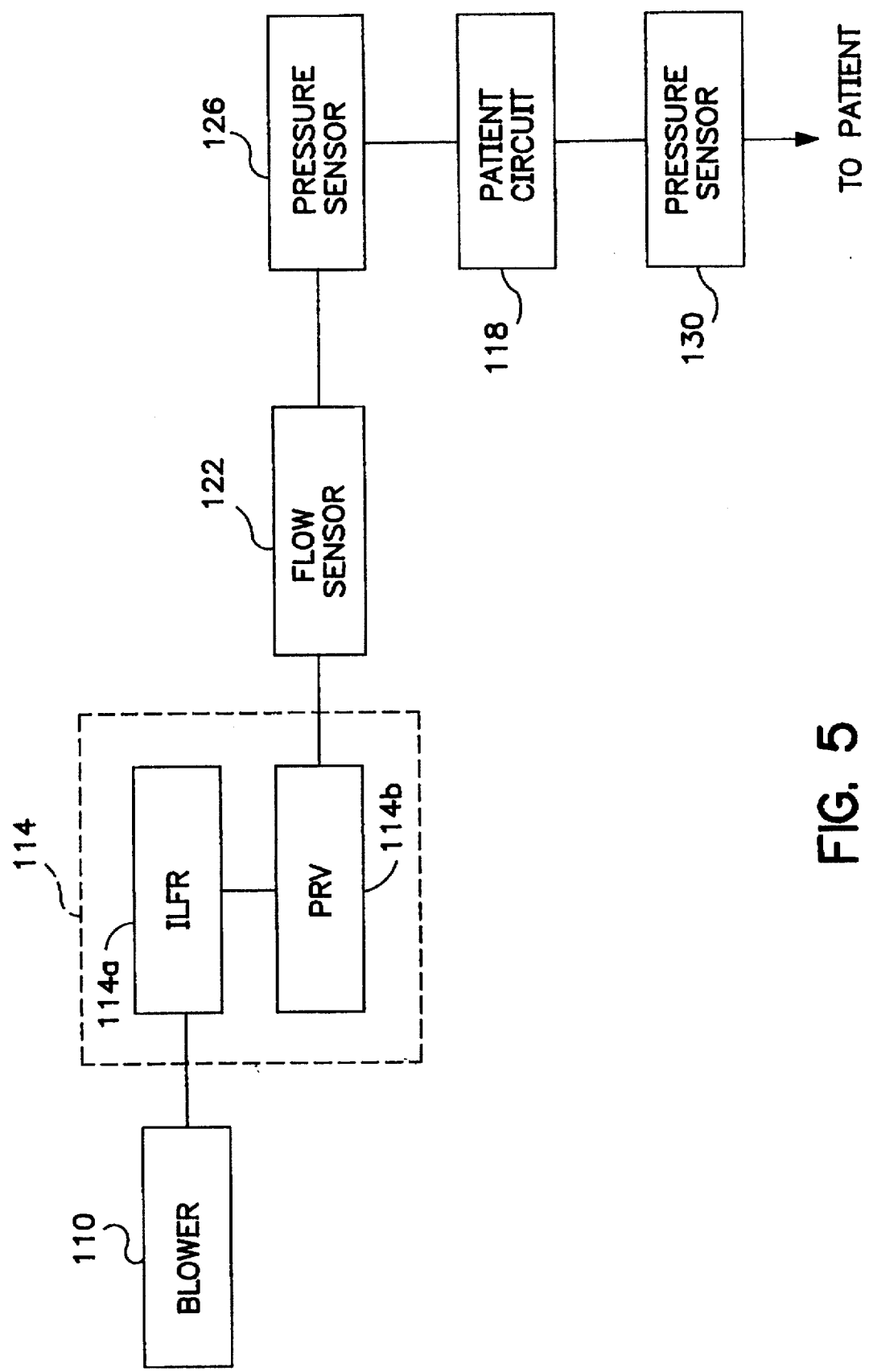
FIG. 5 also schematically illustrates components of a respirator circuit according to at least one preferred embodiment of the present invention.

FIG. 5 illustrates, in accordance with at least one preferred embodiment of the present invention, the provision of two valves 114a and 114b as the aforementioned valving arrangement 114. For the purpose of further discussion, valve 114a, shown as being the valve situated more closely in fluid communication with blower 110, may be termed the "in-line flow restrictor" or the "ILFR" valve, while the valve 114b situated downstream from valve 114a may be termed a "pressure relief valve" or "PRV".

In accordance with a preferred embodiment of the present invention, ILFR 114a will be so configured as to provide a means for restricting flow in the respirator circuit without venting any flow to the ambient atmosphere or other remote location. In contrast, PRV 114b will preferably be configured to operate in the manner of a conventional pressure relief valve, such that it will serve to vent flow to the ambient atmosphere or other selected remote location.

Accordingly, ILFR 114a and PRV 114b will preferably be provided and configured in a manner deemed suitable for the context at hand and, in this sense, can conceivably each be embodied by any arrangements suitable for carrying out their respective above-discussed tasks. A more specific embodiment, however, will be discussed further below.

Figure 5A:
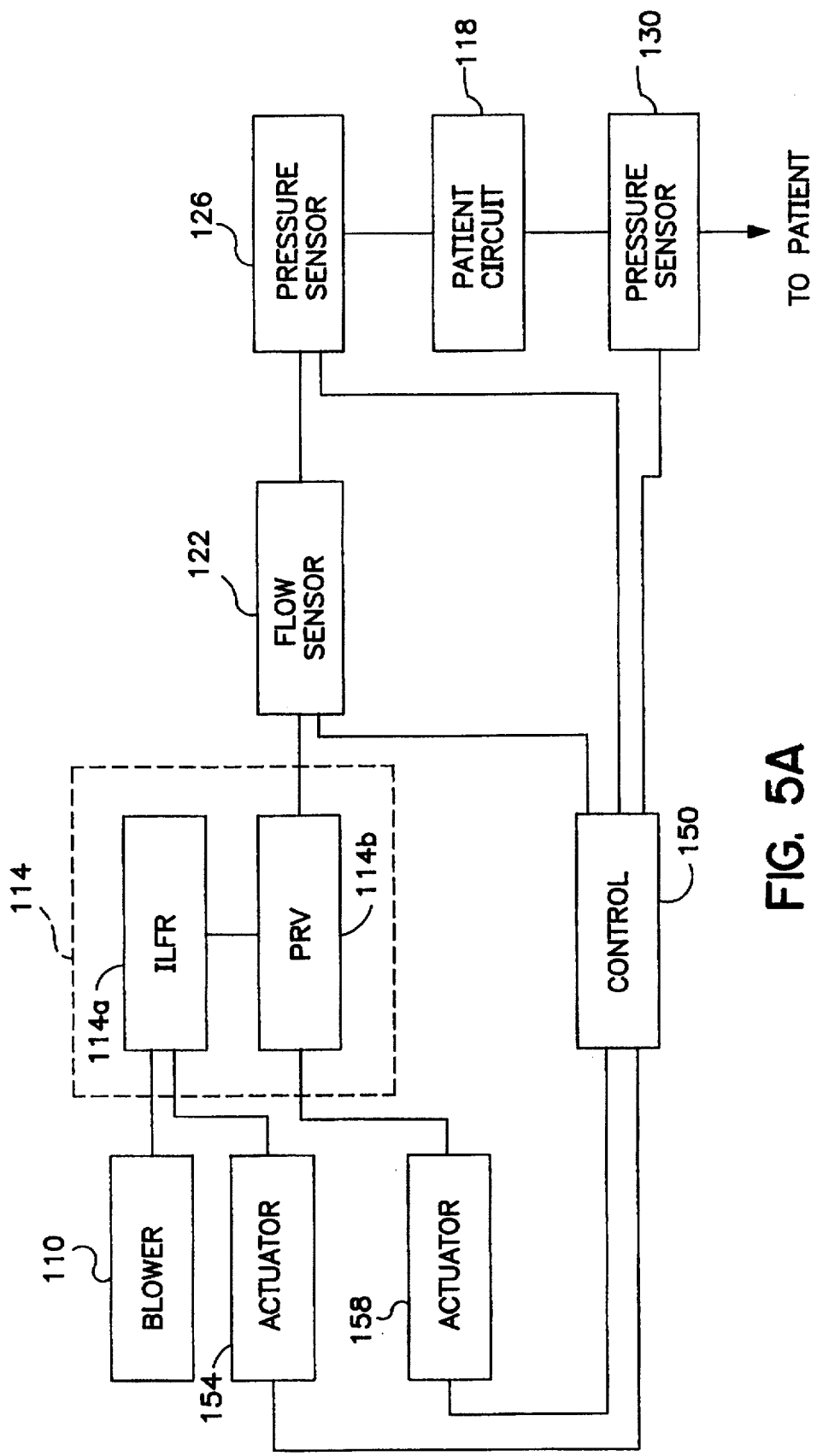
FIG. 5A schematically illustrates essentially the same components as shown in FIG. 5, but also schematically illustrates a control system.

FIG. 5A schematically illustrates the inclusion of a control arrangement 150 which, in accordance with a preferred embodiment of the present invention, may monitor any or all of flow sensor 122, pressure sensor 126 and pressure sensor 130, and, in a manner deemed suitable for the operation at hand, prompt suitable actuators 154 and 158 to respectively activate ILFR 114a and/or PRV 114b so as to control pressure and/or flow to the patient.

As an example, in the context of a "BiPAP" procedure, it may first be assumed that a predetermined "IPAP" pressure (that is, a constant pressure to be administered to the patient during inhalation) is preselected at a suitable console, thereby prompting blower 110 to output at a given motor speed for a given resultant initial "deadhead" pressure. Already, control 150 may preferably prompt ILFR 114a and PRV 114b to each be actuated to respective degrees so as to preferably provide the desired target IPAP pressure to the patient (conceivably as measured by sensor 130) while minimizing the flow that is vented by PRV 114b.

In this respect, it may now be appreciated that ILFR 114a and PRV 114b are each preferably embodied by proportional-type valving schemes that can be essentially continuously adjustable. In the case of ILFR 114a, for example, maximum "closure" of the valve could result in maximally constricted flow, while minimum closure (or maximal "opening") could result in minimally constricted flow. On the other hand, PRV 114b may be embodied in the manner of a conventional pressure relief valve, that is, it will preferably open to varying degrees so as to exhaust varying degrees of flow away from the respirator circuit. Types of proportional valves suitable for these purposes, as well as suitable actuators, would appear to be well-known, and will thus not be further discussed at present. For example it is conceivable to employ in each case a poppet-type valve that is selectively and proportionally actuable by way of a variable electrical current applied to the respective actuator.

The manner of respectively controlling ILFR 114a and PRV 114b will preferably be carried out so as to fulfill the objectives of adequately providing the pressure demanded for or by the patient while minimizing wasted flow that would otherwise be vented through a valve such as pressure relief valve 114b. In this respect, ILFR 114a and PRV 114b can preferably work in tandem, a scenario that can be easily programmed into the control arrangement 150.

Whereas a single pressure relief valve, such as that indicated at 114b, might normally require being open to a significant degree most of the time in order to permit a margin of safety in the event that a high level of air or gas pressure is demanded for or by the patient (as discussed previously in the "Background" section of this disclosure), so as to close to a given degree to increase flow and pressure upon such a demand, it may now be appreciated that ILFR 114a can essentially preclude the need for such extensive "preliminary" opening of the PRV 114b. More particularly, the ILFR 114a can serve to restrict flow and pressure initially, essentially with a similar effect as a conventional pressure relief valve as just described but without the added disadvantage that flow is unnecessarily vented away from the respirator circuit.

It will be appreciated that the possible schemes of operation of an ILFR 114a and PRV 114b according to the present invention cover a wide range, all with the effect of minimizing wasted flow in comparison with previous single pressure-relief valve systems. In one embodiment, the PRV 114b may initially be open to a given degree so as to vent flow during times when excess pressure is not demanded. Simultaneously, ILFR 114a may be closed to a given degree (i.e. in a position to restrict flow to a given degree) during such times. Depending on the control scheme adopted, it is conceivable to adjust either or both of the ILFR 114a and the PRV 114b when a demand for increased pressure is detected or prompted. In one embodiment of the present invention, this could be accomplished by continually opening the ILFR 114a while allowing the PRV 114b to remain at the same position as previously. Consequently, if the ILFR 114a were to open to a maximal degree in the presence of a particularly acute pressure demand, the PRV 114b could be prompted to "kick in" and subsequently close so as to augment the added pressure and flow provided by the maximal opening of the ILFR 114a. Alternatively, a reverse scenario could take place, in which pressure regulation during "normal" periods (i.e. during periods in which not acutely high pressure levels are demanded by or for the patient) could be effected by the PRV 114b, followed by augmentation by the ILFR 114a when needed. Either alternative may conceivably be chosen with a view to accomplishing any particularly desired objectives (for example, the latter alternative scenario could be adopted if the venting of excess flow is not seen as detrimental and if, for example, the accumulation of backpressure in the blower is desired to be prevented).

Upon an exhalation by the patient, by using appropriate sensors and circuitry such as that described with reference to FIGS. 1–3, it is conceivable to exact a situation in which the ILFR 114a will maximally close and the PRV 114b will maximally open, so as to permit the exhaled air or gas, now travelling back through the respirator circuit in the direction towards blower 110, to be vented away through PRV 114b.

Figure 6:
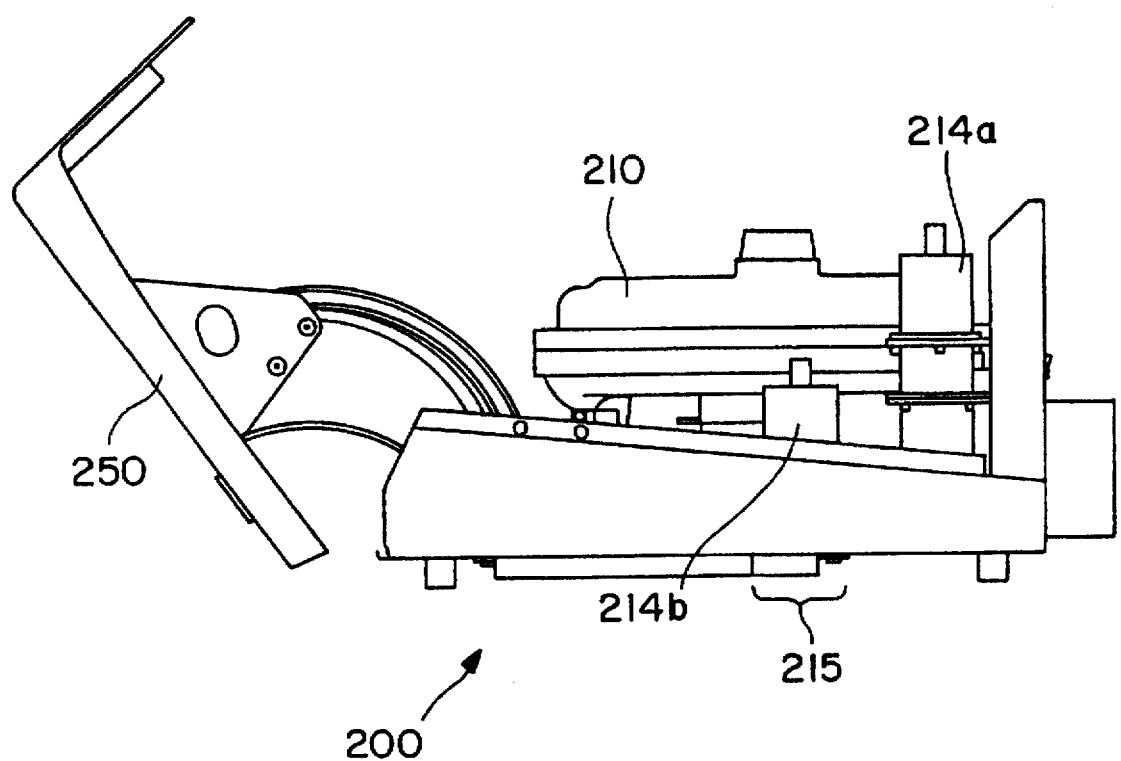
FIG. 6 is an elevational view of main portion of a respiration device according to an embodiment of the present invention.
Figure 7:
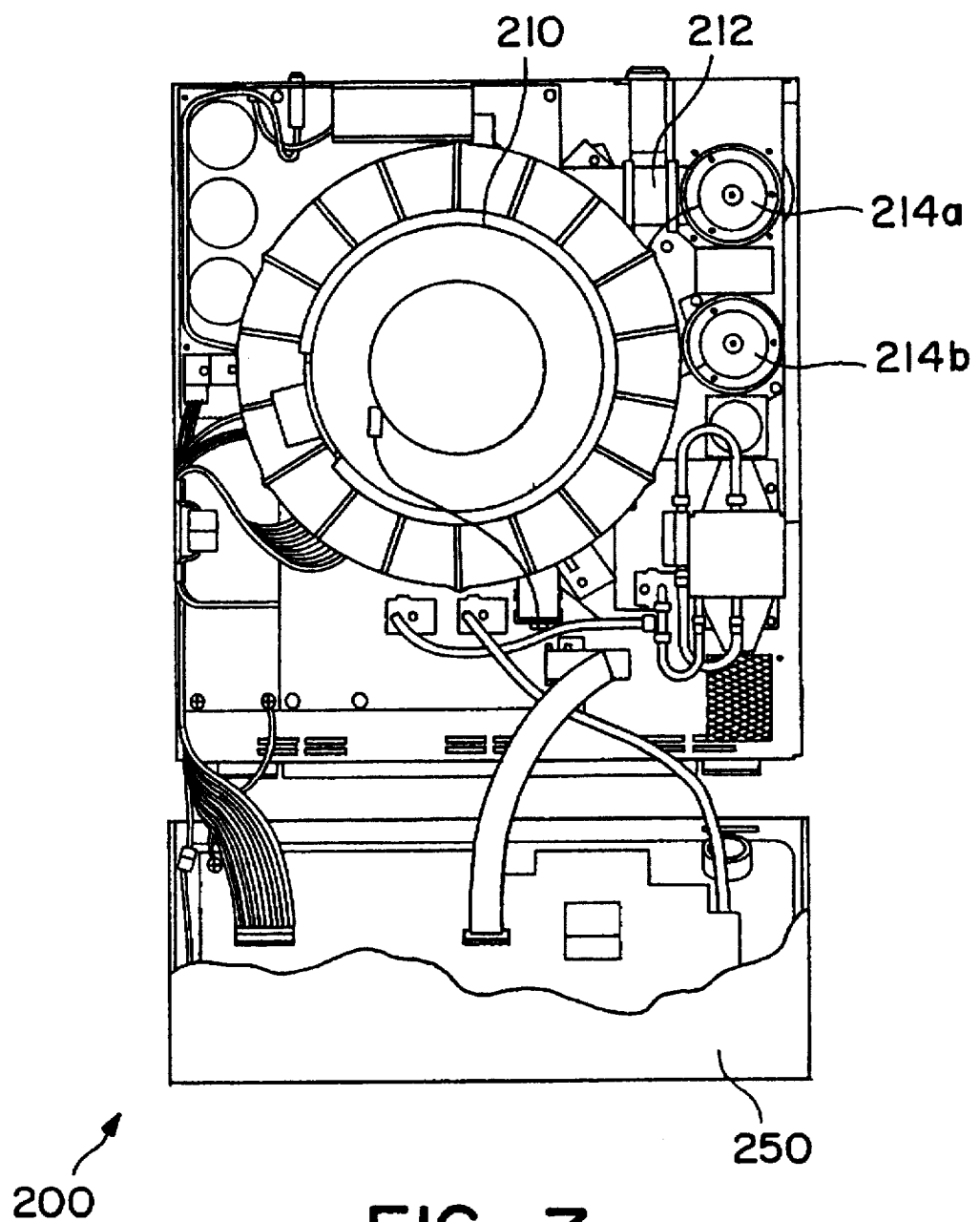
FIG. 7 is a plan view of the respiration device illustrated in FIG. 6.

FIGS. 6 and 7 illustrate a general layout of a respiration apparatus 200 that may be employed in accordance with the embodiments of the present invention. Particularly, a suitable conduit 212 may preferably lead from blower 210 into ILFR 214a, which in turn will direct flow to PRV 214b. As shown in FIG. 6, a region 215 underneath PRV 214b may preferably serve as the region from which flow is exhausted or bled out of the apparatus 200 into the ambient atmosphere. Also shown in FIGS. 6 and 7 is a removable cover 250.

Figure 8:
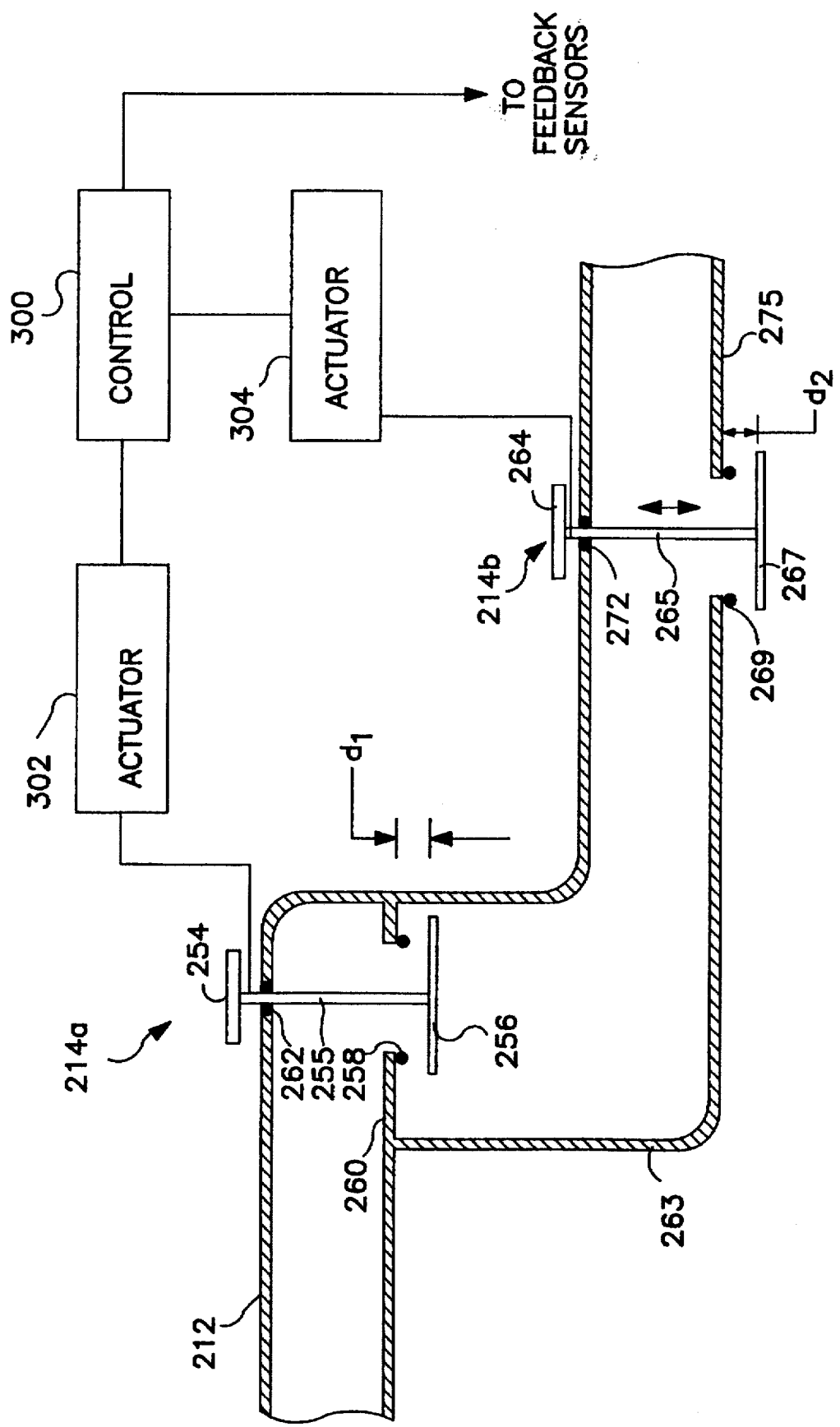
FIG. 8 is a detailed illustration of a valving arrangement according to an embodiment of the present invention.

FIG. 8 shows a more detailed illustration of valving arrangements 214a and 214b that may be employed in accordance with the present invention.

Preferably, ILFR 214a may include a head portion 254, a rod portion 255 and a piston or disc portion 256. As illustrated, conduit 212 may preferably lead towards ILFR 214a in such a manner that, with piston/disc portion 256 displaced maximally upward, such that it rests against suitably configured and oriented stop or stops 258, flow from the blower will be maximally restricted at this point. With piston/disc portion 256 displaced maximally downward, flow from the blower will be minimally restricted. Preferably, a suitable sealing arrangement 262 may be provided about rod portion 255 at its region of interaction with conduit 212.

To achieve maximal opening of ILFR 214a, it is conceivable to permit the striking of head 254 against the exterior of conduit 212 to serve as a limit position. Alternatively, it is conceivable to provide, within conduit 263 (i.e. that conduit portion that extends downwardly from ILFR 214a), suitable stops that will cease downward movement of piston/disc 256 at a predetermined position.

Preferably, even with ILFR 214a maximally closed, there will preferably be a provision for some minimal degree of flow to progress past ILFR 214a. Thus, in one embodiment of the present invention, there could be provided a given number of stops 258, spaced circumferentially at given distances from one another, that would still permit a minimal degree of flow with piston/disc portion 256 in a maximally upward position. Alternatively, piston/disc portion 256 could be embodied by a slotted disc that would permit such minimal flow. Other arrangements, including other types of stops provided in the interior of conduit 263, are certainly conceivable within the scope of the present invention.

Conduit portion 263 may preferably lead from ILFR 214a to PRV 214b, which itself may include a head portion 264, a rod portion 265 and a piston or disc portion 267. As illustrated, with piston/disc portion 267 displaced maximally upward, such that it rests against suitably configured and oriented stop or stops 269, flow will be minimally vented (with a concomitant increased pressure). Further, with piston/disc portion 267 displaced maximally downward, flow will be maximally vented (with a concomitant reduced pressure). Preferably, a suitable sealing arrangement 262 may be provided about rod portion 255 at its region of interaction with conduit 212.

With the provision of a control arrangement 300, itself linked to system feedback sensors of the type described and alluded to variously throughout this disclosure, and also of suitable actuators 302 and 304 (respectively dedicated to ILFR 214a and PRV 214b), it will be appreciated that respective opening distances $d_1$ and $d_2$ of ILFR 214a and PRV 214b can be controlled to achieve the inventive pressure and flow regulation discussed heretofore.

Herebelow, a brief discussion is provided of one possible mode of operation according to a preferred embodiment of the present invention.

Naturally, at the outset of a procedure in which a patient is to utilize a respiration device according to the present invention, he or she will first put on a mask that has been provided. For the present discussion, it can be assumed that the mask will represent part of a "non-invasive" treatment, in which the patient does not accept any respirator components internally.

With the respiratory device being turned on, in accordance with at least one preferred embodiment of the present invention, either the patient or clinician may then establish the "IPAP" and "EPAP" levels discussed and alluded to hereinabove if a "bi-level" apparatus is being used. Alternatively, if an apparatus is being used that employs a more variable scheme of pressure provision, the patient or clinician will either activate a stored program that expressly varies pressures over time or possibly activate a scheme that depends on instantaneous patient monitoring. Subsequently, the patient or clinician may actually activate the respiration process by utilizing an appropriate switch for starting the blower 110.

The patient will then inhale, and in view of the sensing circuitry described hereinabove, the machine will be alerted to provide the appropriate pressure to the patient. Inasmuch as the base or "static" flow now provided by the blower 110 will necessarily be augmented by the patient's inward breath, the effective flow rate of air or gas through the patient's mask into the patient's airway will represent an increase over the initial flow level provided by the blower.

As discussed hereinabove, it would have been typical, in the past, for any excess flow to be vented at any one of a number of suitable points along the respiration circuit. "Excess flow", in this context, is the difference between the required blower circuit flow (required to produce the commanded patient circuit pressure) and the actual flow taken in by the patient. However, in accordance with at least one preferred embodiment of the present invention, the ILFR 114a, with the aid of the aforementioned feedback circuitry, will preferably be adjusted in such a manner as to restrict flow from the blower itself and, if necessary, concomitantly alter the blower output so as to still provide the desired IPAP pressure. Of course, during this time, the PRV 114b may also be controllably linked with the ILFR 114a by way of a control arrangement such as those discussed heretofore. Thus, by the time the air flow reaches the patient, the target pressure will be present with only minimal wasted flow.

Upon completion of an inhalation breath, and at the outset of an exhalation breath by the patient, the sensing circuitry described and alluded to hereinabove will appropriately alert the control circuitry into providing another pressure, possibly a so-called EPAP pressure. At this point, in accordance with at least one preferred embodiment of the present invention, essentially two actions may be effected. First, the ILFR will preferably close as much as possible (although it is conceivable to maintain a minimum opening with the ILFR 114a, possibly by utilizing mechanical stops or the like). In so doing, it will help prepare for the next stage, in which the patient's exhaled breath will return through the respiration circuit up to the PRV 114b. In a known manner, the PRV 114b will be opened in such a manner as to permit the patient's returning breath to be exhausted to the ambient atmosphere or to another predetermined location. At this point, the ILFR 114a will be used for the purpose of controlling pressure while minimzing flow from the blower, a condition that can easily be programmed into the control circuitry.

Once the patient's exhalation breath is complete and he or she then begins a new inhalation breath, the process described hereinabove will again be repeated, wherein a pressure such as an "IPAP" pressure will again be effected by blower 110. Possibly, ILFR 114a will be continuously adjusted, in response to pressures demanded by the patient, until such a time that demand is so acute that the negligibly opened PRV 114b will close, to increase pressure.

It will be appreciated that a valving arrangement according to the present invention will be capable of accommodating significantly high pressure and flow, even in the presence of a highly restrictive patient circuit 118. It has been found that valving arrangements, such as the combination of ILFR 114a and PRV 114b disclosed herein, are capable of controlling a deadhead pressure of 60 cm $H_2O$ or higher.

If not otherwise stated herein, it may be assumed that all components and/or processes described heretofore may, if appropriate, be considered to be interchangeable with similar components and/or processes disclosed elsewhere in the specification, unless an indication is made to the contrary.

It should be appreciated that the apparatus and methods of the present invention may be configured and conducted as appropriate for the application. The embodiments described above are to be considered in all respects only as illustrative and not restrictive. The scope of the invention is defined by the following claims rather than by the foregoing description. All changes which come within the meaning and range of equivalency of the claims are to be embraced within their scope.

What is claimed is:

1. Apparatus for delivering pressurized gas to the airway of a patient, said apparatus comprising:

gas flow generator means for providing a flow of said gas;

conduit means for delivery of said gas flow to the airway of the patient;

means for controlling the pressure of said gas flow delivered to the airway of the patient;

said controlling means comprising:

means for restricting said gas flow in said conduit means prior to its being delivered to the airway of the patient;

means for venting gas; and means for selectively actuating at least said restricting means in a manner to substantially minimize the quantity of vented gas.

2. The apparatus according to claim 1, wherein said actuating means comprises means for selectively actuating said restricting means and said venting means in a manner to substantially minimize the quantity of vented gas.

3. The apparatus according to claim 2, wherein said actuating means comprises means for separately and independently actuating said restricting means and said venting means with respect to one another.

4. The apparatus according to claim 2, wherein said venting means comprises at least one proportionally actuable element for proportionally venting a portion of said gas flow away from said conduit means.

5. The apparatus according to claim 2, wherein said restricting means comprises at least one proportionally actuable element for proportionally restricting said gas flow in said conduit means.

6. The apparatus according to claim 2, wherein said venting means comprises at least one proportionally actuable element for proportionally venting a portion of said gas flow away from said conduit means.

7. The apparatus according to claim 1, wherein said controlling means if further for maintaining the pressure of said gas flow delivered to the airway of the patient simultaneously as a function of at least:

the restriction of said gas flow by said restricting means; and the quantity of vented gas.

8. The apparatus according to claim 7, wherein said venting means comprises means for venting gas flow away from said conduit means.

9. The apparatus according to claim 8, wherein:

said controlling means is further for maintaining the pressure of said gas flow delivered to the airway of the patient as inversely proportional to the restriction of said gas flow by said restricting means; and inversely proportional to the quantity of gas flow vented away from said conduit means by said venting means.

10. The apparatus according to claim 7, wherein said restricting means comprises an in-line flow restricting arrangement comprising means for restricting said gas flow in said conduit means without venting any gas flow away from said conduit means.

11. The apparatus according to claim 10, wherein:

said venting means comprises a pressure relief valve arrangement actuable between a first, maximally open state, whereby maximal venting of said gas flow away from said conduit means takes place through said pressure relief valve arrangement, and a second, maximally closed state, whereby minimal venting of said gas flow away from said conduit means takes place through said pressure relief valve arrangement;

said in-line flow restrictor arrangement is actuable between a first state, whereby maximal restriction of said gas flow takes place at said in-line flow restrictor arrangement, and a second state, whereby minimal restriction of said gas flow takes place at said in-line flow restrictor arrangement; and said actuating means comprises means for selectively increasing the pressure of said gas flow delivered to the airway of the patient via at least one of the following steps a) and b):

a) actuating said pressure relief valve arrangement generally away from its first state and generally towards its second state; and b) actuating said in-line flow restrictor arrangement generally away from its second state and generally towards its first state.

12. The apparatus according to claim 11, wherein said actuating means comprises means for performing said steps a) and b) in a manner to minimize the quantity of gas flow vented away from said conduit means prior to its being delivered to the airway of the patient.

13. The apparatus according to claim 12, comprising: wherein said conduit means further comprises a first conduit portion, in which said in-line flow restrictor arrangement is disposed;

a second conduit portion, in which said pressure relief valve arrangement is disposed; and a connecting conduit portion connected between said first and second conduit portions;

wherein said first conduit portion, said connecting conduit portion and said second conduit portion are connected directly and uninterruptedly in series with one another.

14. The apparatus according to claim 12, wherein said actuating means comprises means for varying the gas flow pressure via feedback control, the feedback control including at least one of: gas flow rate feedback control and gas pressure feedback control.

15. In apparatus for delivering pressurized gas to the airway of a patient, such apparatus comprising gas flow generator means for providing a flow of said gas and conduit means for delivery of said gas flow to the airway of the patient; means for controlling the pressure of said gas flow delivered to the airway of the patient, said controlling means comprising:

means for restricting said gas flow in said conduit means prior to its being delivered to the airway of the patient;

means for selectively venting gas; and means for selectively actuating at least said restricting means in a manner to substantially minimize the quantity of vented gas.

16. In apparatus according to claim 15, wherein the pressure of said gas flow delivered to the airway of the patient is simultaneously a function of at least:

the restriction of said gas flow by said restricting means; and the quantity of vented gas.

17. In apparatus according to claim 16, wherein said restricting means comprises an in-line flow restricting arrangement comprising means for restricting said gas flow in said conduit means without venting any gas flow away from said conduit means.

18. In apparatus according to claim 17, wherein said venting means comprises means for venting gas flow away from said conduit means.

19. In apparatus according to claim 18, wherein:

said venting means comprises a pressure relief valve arrangement actuable between a first, maximally open state, whereby maximal venting of said gas flow away from said conduit means takes place through said pressure relief valve arrangement, and a second, maximally closed state, whereby minimal venting of said gas flow away from said conduit means takes place through said pressure relief valve arrangement;

said in-line flow restrictor arrangement is actuable between a first state, whereby maximal restriction of said gas flow takes place at said in-line flow restrictor arrangement, and a second state, whereby minimal restriction of said gas flow takes place at said in-line flow restrictor arrangement; and said actuating means comprises means for selectively increasing the pressure of said gas flow delivered to the airway of the patient via at least one of the following steps a) and b):

a) actuating said pressure relief valve arrangement generally away from its first state and generally towards its second state; and b) actuating said in-line flow restrictor arrangement generally away from its second state and generally towards its first state.

20. In apparatus according to claim 19, wherein said actuating means comprises means for performing said steps a) and b) in a manner to minimize the quantity of gas flow vented away from said conduit means prior to its being delivered to the airway of the patient.

21. Method of controlling the pressure of gas flow delivered to the airway of a patient comprising the steps of: providing an apparatus for delivering pressurized gas to the airway of a patient, such apparatus comprising gas flow generator means for providing a flow of said gas and conduit means for delivery of said gas flow to the airway of the patient;

restricting said gas flow in said conduit means prior to its being delivered to the airway of the patient;

venting gas; and selectively controlling at least the restriction of gas flow in a manner to substantially minimize the quantity of vented gas.

22. The method according to claim 21, wherein:

said providing step further comprising providing a pressure relief valve arrangement for undertaking said venting step, said pressure relief valve arrangement being actuable between a first, maximally open state, whereby maximal venting of said gas flow away from said conduit means takes place through said pressure relief valve arrangement, and a second, maximally closed state, whereby minimal venting of said gas flow away from said conduit means takes place through said pressure relief valve arrangement;

and an in-line flow restricting arrangement for undertaking said restricting step, said in-line flow restricting arrangement being actuable between a first state, whereby maximal restriction of said gas flow takes place at said in-line flow restrictor arrangement, and a second state, whereby minimal restriction of said gas flow takes place at said in-line flow restrictor arrangement; and said step of selectively actuating comprises selectively increasing the pressure of said gas flow delivered to the airway of the patient via at least one of the following steps a) and b):

a) actuating said pressure relief valve arrangement generally away from its first state and generally towards its second state; and b) actuating said in-line flow restrictor arrangement generally away from its second state and generally towards its first state;

wherein said at least one of said steps a) and b) is performed in a manner to minimize the quantity of gas flow vented away from said conduit means prior to its being delivered to the airway of the patient.

23. The method according to claim 21, further comprising the step of maintaining the pressure of said gas flow delivered to the airway of the patient simultaneously as a function of at least:

the restriction of said gas flow; and the quantity of vented gas.

24. The method according to claim 23, wherein said venting step comprises venting gas flow away from said conduit means.

25. The method according to claim 24, wherein:

the pressure of said gas flow delivered to the airway of the patient is inversely proportional to the restriction of said gas flow by said restricting means; and the pressure of said gas flow delivered to the airway of the patient is inversely proportional to the quantity of gas flow vented away from said conduit means by said venting means.

* * * * *